(12) United States Patent
Hara et al.

(10) Patent No.: US 8,222,007 B2
(45) Date of Patent: Jul. 17, 2012

(54) L-GLUTAMIC ACID PRODUCING BACTERIUM AND A METHOD FOR PRODUCING L-GLUTAMIC ACID

(75) Inventors: Yoshihiko Hara, Kawasaki (JP); Hiroshi Izui, Kawasaki (JP)

(73) Assignee: Ajinomoto Co., Inc., Tokyo (JP)

( * ) Notice: Subject to any disclaimer, the term of this patent is extended or adjusted under 35 U.S.C. 154(b) by 677 days.

(21) Appl. No.: 12/388,133

(22) Filed: Feb. 18, 2009

(65) Prior Publication Data
US 2009/0215131 A1 Aug. 27, 2009

Related U.S. Application Data

(63) Continuation of application No. PCT/JP2007/066327, filed on Aug. 16, 2007.

(60) Provisional application No. 60/823,921, filed on Aug. 30, 2006.

(30) Foreign Application Priority Data

Aug. 18, 2006 (JP) ................................. 2006-223288

(51) Int. Cl.
| C12P 13/14 | (2006.01) |
| C12P 13/04 | (2006.01) |
| C12N 1/20 | (2006.01) |
| C12N 15/74 | (2006.01) |
| C12N 9/12 | (2006.01) |

(52) U.S. Cl. ..................... 435/110; 435/106; 435/252.1; 435/252.3; 435/471; 435/477; 435/194

(58) Field of Classification Search .................. 435/110, 435/106, 252.1, 252.3, 471, 477, 194
See application file for complete search history.

(56) References Cited

U.S. PATENT DOCUMENTS

| 3,220,929 A | 11/1965 | Kinoshita et al. |
| 3,563,857 A | 2/1971 | Oki et al. |
| 5,378,616 A | 1/1995 | Tujimoto et al. |
| 5,393,671 A | 2/1995 | Tujimoto et al. |
| 6,197,559 B1 | 3/2001 | Moriya et al. |
| 7,247,459 B1 | 7/2007 | Izui et al. |
| 7,344,874 B2 | 3/2008 | Hara et al. |
| 2001/0019836 A1 | 9/2001 | Moriya et al. |
| 2003/0119153 A1 | 6/2003 | Moriya et al. |
| 2004/0082040 A1 | 4/2004 | Rieping et al. |
| 2006/0040365 A1 | 2/2006 | Kozlov et al. |
| 2006/0088919 A1 | 4/2006 | Rybak et al. |
| 2006/0246552 A1 | 11/2006 | Hara et al. |

FOREIGN PATENT DOCUMENTS

| EP | 0 955 368 | 11/1999 |
| JP | 32-9393 | 11/1957 |
| JP | 5-244970 | 9/1993 |
| JP | 2000-189157 | 7/2000 |
| JP | 2000-189169 | 7/2000 |
| JP | 2000-189175 | 7/2000 |
| WO | WO01/05939 | 1/2001 |
| WO | WO 01/05939 | * 1/2001 |
| WO | WO 03/074719 | * 9/2003 |
| WO | WO2008/020654 | 2/2008 |

OTHER PUBLICATIONS

Martinez-Garcia et al. 2001. Arch Microbiol, 175:395-404.*
Anderson et al., Identification and characterization of the Erwinia . . . J. Bacteriol., 1998, vol. 180(24): 6789-6792.*
Broun et al., Catalytic plasticity of fatty acid modification enzymes underlying chemical diversity of plant lipids. Science, 1998, vol. 282: 1315-1317.*
Devos et al., Practical limits of function prediction. Proteins: Structure, Function, and Genetics. 2000, vol. 41: 98-107.*
Kisselev L., Polypeptide release factors in prokaryotes and eukaryotes: same function, different structure. Structure, 2002, vol. 10: 8-9.*
Seffernick et al., Melamine deaminase and Atrazine chlorohydrolase: 98 percent identical but functionally different. J. Bacteriol., 2001, vol. 183 (8): 2405-2410.*
Whisstock et al., Prediction of protein function from protein sequence. Q. Rev. Biophysics., 2003, vol. 36 (3): 307-340.*
Wishart et al., A single mutation converts a novel phosphotyrosine binding domain into a dual-specificity phosphatase. J. Biol. Chem., 1995, vol. 270(45): 26782-26785.*
Witkowski et al., Conversion of b-ketoacyl synthase to a Malonyl Decarboxylase by replacement of the active cysteine with glutamine. Biochemistry, 1999, vol. 38: 11643-11650.*
Colland, F., et al., "The interaction between $\sigma^s$, the stationary phase $\sigma$ factor, and the core enzyme of *Escherichia coli* RNA polymerase," Genes to Cells 2002;7:233-247.
Kikuchi, M., et al., Biotechnology of Amino Acid Production, progress in industrial microbiology, vol. 24, pp. 101-116, Kodansha Ltd., Tokyo (Corresponding to Kunihiko Akashi et al., "Amino acid fermentation", pp. 195-215, 1986, Japan Scientific Societies Press).
Lee, I.S., et al., "The stationary-phase sigma factor $\sigma^s$ (RpoS) is required for a sustained acid tolerance response in virulent *Salmonella typhimurium*," Mol. Microbiol. 1995;17(1):155-167.
Rajkumari, K., et al., "Effects of H-NS and Potassium Glutamate on $\sigma^s$—and $\sigma^{70}$—Directed Transcription In Vitro from Osmotically Regulated P1 and P2 Promoters of *proU* in *Escherichia coli*," J. Bacteriol. 1996;178(14):4176-4181.
International Preliminary Report on Patentability for PCT Patent App. No. PCT/JP2007/066327 (Mar. 5, 2009).

* cited by examiner

*Primary Examiner* — Ganapathirama Raghu
(74) *Attorney, Agent, or Firm* — Shelly Guest Cermak; Cermak Nakajima LLP

(57) ABSTRACT

The present invention describes an L-glutamic acid-producing bacterium which belongs to the genus *Pantoea*, *Enterobacter*, *Klebsiella* or *Erwinia*, wherein the bacterium has been modified by gene recombination to inactivate the rpoS gene. A method is also described for culturing the bacterium in a medium to cause accumulation of L-glutamic acid in the medium, and collecting L-glutamic acid from the medium.

6 Claims, 3 Drawing Sheets

L-GLUTAMIC ACID PRODUCING BACTERIUM AND A METHOD FOR PRODUCING L-GLUTAMIC ACID

This application is a continuation under 35 U.S.C. §120 of PCT/JP2007/066327, filed Aug. 16, 2007, which claims priority under 35 U.S.C. §119 to Japanese Patent Application No. 2006-223288, filed on Aug. 18, 2006, and U.S. Provisional Patent Application No. 60/823,921, filed Aug. 30, 2006, all of which are incorporated by reference. The Sequence Listing filed electronically herewith is also hereby incorporated by reference in its entirety (File Name: US-304_Seq_List; File Size: 11 KB; Date Created: Feb. 18, 2009).

BACKGROUND OF THE INVENTION

1. Field of the Invention

The present invention relates to an L-glutamic acid producing bacterium and a method for producing L-glutamic acid. L-glutamic acid is widely used as a raw material in the making of seasonings and so forth.

2. Brief Description of the Related Art

L-glutamic acid is typically produced by fermentation utilizing the so-called coryneform bacteria, which belong to the genus *Brevibacterium, Corynebacterium,* or *Microbacterium,* or mutant strains thereof (Kunihiko Akashi et al., "Amino acid fermentation", pp. 195-215, 1986, Japan Scientific Societies Press). Methods for producing L-glutamic acid by fermentation using other bacterial strains include using a microorganism belonging to the genus *Bacillus, Streptomyces, Penicillium,* or the like (U.S. Pat. No. 3,220,929), using a microorganism belonging to the genus *Pseudomonas, Arthrobacter, Serratia, Candida* or the like (U.S. Pat. No. 3,563,857), using a microorganism belonging to the genus *Bacillus, Pseudomonas, Serratia, Aerobacter aerogenes* (currently referred to as *Enterobacter aerogenes*) or the like (Japanese Patent Publication (KOKOKU) No. 32-9393), using a mutant strain of *Escherichia coli* (Japanese Patent Laid-open (KOKAI) No. 5-244970), and so forth. In addition, methods for producing L-glutamic acid using a microorganism belonging to the genus *Klebsiella, Erwinia, Pantoea,* or *Enterobacter* have also been disclosed (Japanese Patent Laid-open Nos. 2000-106869, 2000-189169, and 2000-189175). Moreover, it is known that the L-glutamic acid producing ability of *Escherichia* bacteria and coryneform bacteria can be improved by deleting the rpoS gene (WO01/05939).

The RpoS protein (also known as "sigma S factor") encoded by the rpoS gene is not only known as a stationary phase-specific sigma factor, but also as a sigma factor which responds to various kinds of stress resulting in the control of various genetic expressions. More specifically, the sigma S factor plays a central role in acquisition of acid resistance, and it is reported that the survival rate of rpoS gene-deficient strains dramatically decreases under acidic conditions (Mol. Microbiol., 1995 Jul., 17(1):155-67). However, the majority of the research on acid resistance in microorganisms typically focuses on survival rate under acidic conditions, and there are no reports about growth under acidic conditions. In addition, growth of rpoS-deficient strains under acidic conditions has not been investigated to date.

SUMMARY OF THE INVENTION

The present invention describes a bacterium which can efficiently produce L-glutamic acid, and a method for efficiently producing L-glutamic acid by using the bacterium.

The present invention was achieved by improving the fermentation yield of L-glutamic acid, and improving the growth of an L-glutamic acid-producing bacteria under acidic conditions when the rpoS gene, which encodes the sigma S factor of RNA polymerase, was inactivated.

It is an aspect of the present invention to provide an L-glutamic acid-producing bacterium which belongs to a genus selected from the group consisting of *Pantoea, Enterobacter, Klebsiella,* and *Erwinia,* wherein the bacterium has been modified by gene recombination so that the rpoS gene is inactivated.

It is a further aspect of the present invention to provide the bacterium as described above, wherein the rpoS gene is inactivated by a method selected from the group consisting of reducing the expression of the rpoS gene, disrupting the rpoS gene, and combinations thereof.

It is a further aspect of the present invention to provide the bacterium as described above, wherein the rpoS gene encodes a protein selected from the group consisting of:

(A) the protein comprising the amino acid sequence of SEQ ID NO: 2, and (B) the protein comprising the amino acid sequence of SEQ ID NO: 2, but which includes substitutions, deletions, insertions, or additions of one or several amino acid residues and which has sigma S factor activity of RNA polymerase.

It is a further aspect of the present invention to provide the bacterium as described above, wherein the rpoS gene is selected from the group consisting of:

(a) the DNA comprising the nucleotide sequence of SEQ ID NO: 1, and (b) a DNA which is able to hybridize with a sequence complementary to the nucleotide sequence of SEQ ID NO: 1, or a probe that can be prepared from the nucleotide sequence, under stringent conditions, and encodes a protein having sigma S factor activity of RNA polymerase.

It is a further aspect of the present invention to provide a method for producing L-glutamic acid comprising culturing the aforementioned bacterium in a medium, and collecting L-glutamic acid from the medium.

It is a further aspect of the present invention to provide the method as described above, wherein the bacterium is cultured at pH 3 to 5.

It is a further aspect of the present invention to provide the method as described above, wherein L-glutamic acid accumulates and precipitates in the medium during the culture.

It is a further aspect of the present invention to provide a method for improving the growth of an L-glutamic acid-producing microorganism under acidic conditions comprising inactivating the rpoS gene of the microorganism by gene recombination.

It is a further aspect of the present invention to provide the method as described above, wherein the microorganism belongs to a genus selected from the group consisting of *Pantoea, Enterobacter, Serratia, Klebsiella,* and *Erwinia.*

DESCRIPTION OF THE PREFERRED EMBODIMENTS

Figure 1:
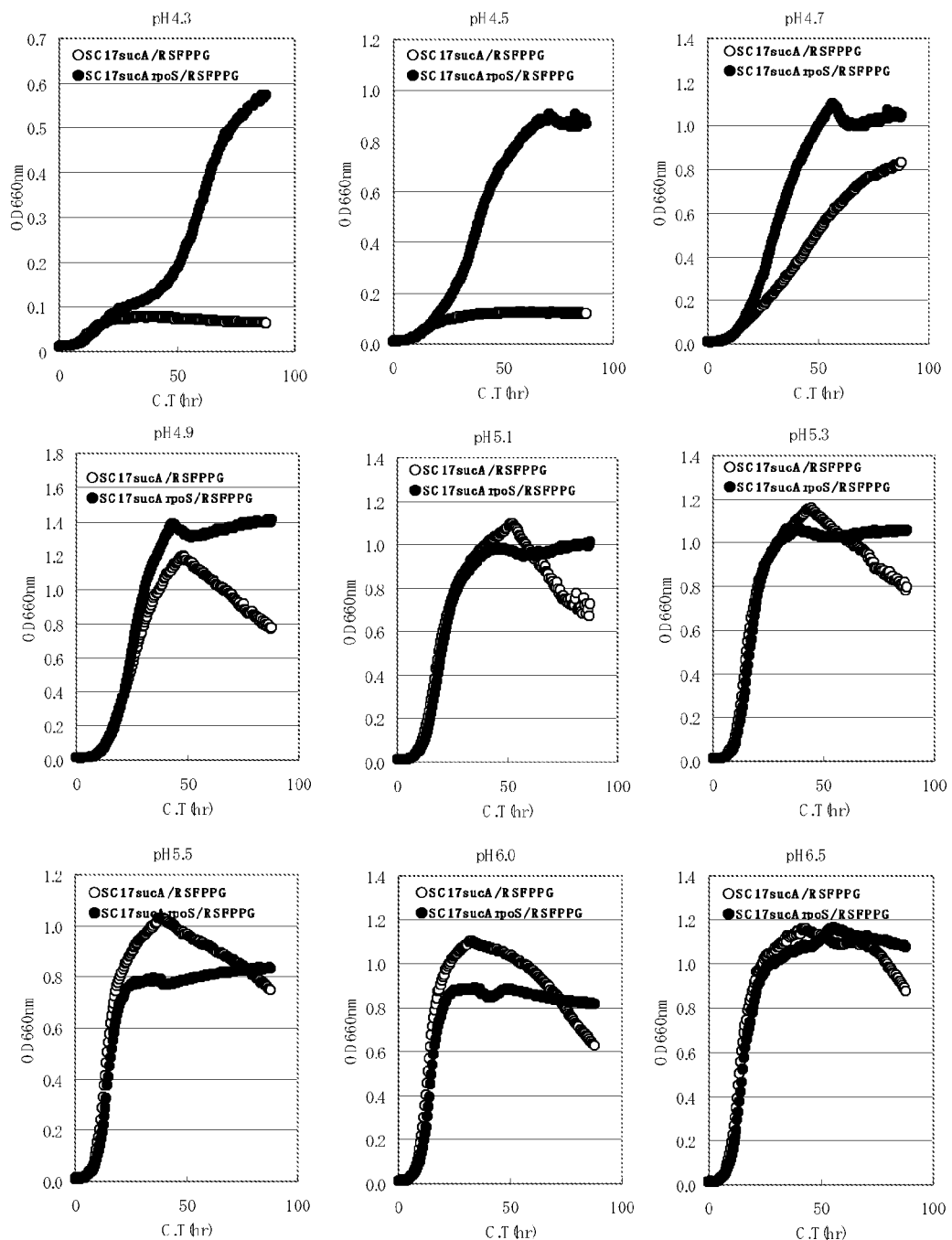
FIG. 1 shows growth of the rpoS-deficient strain under acidic conditions.

The present invention is described in detail below.

<1> L-Glutamic Acid-Producing Bacterium Ntion

The bacterium belongs to the genus *Pantoea, Enterobacter, Klebsiella* or *Erwinia,* has the ability to produce L-glutamic acid, and has been modified by gene recombination to inactivate the rpoS gene.

The term "ability to produce L-glutamic acid (L-glutamic acid-producing ability)" refers to the ability to produce L-glutamic acid and cause accumulation of L-glutamic acid in a medium or cells of the bacterium to such a degree that L-glutamic acid can be collected from the medium or cells when the bacterium is cultured in the medium. The ability to produce L-glutamic acid in the bacterium may be a native ability, or may be imparted by modifying the bacterium using mutagenesis or recombinant DNA techniques.

The bacterium of the present invention preferably grows at a low pH, especially pH 3 to 5.

In particular, *Pantoea* bacteria, *Erwinia* bacteria, and *Enterobacter* bacteria are all classified as γ-proteobacteria, and they are taxonomically very close to one another (J. Gen. Appl. Microbiol., December 1997, 43(6), 355-361; International Journal of Systematic Bacteriology, October 1997, pp. 1061-1067). In recent years, some bacteria belonging to the genus *Enterobacter* were reclassified as *Pantoea agglomerans, Pantoea dispersa*, or the like, on the basis of DNA-DNA hybridization experiments etc. (International Journal of Systematic Bacteriology, July 1989, 39(3), p. 337-345). Furthermore, some bacteria belonging to the genus *Erwinia* were re-classified as *Pantoea ananas* or *Pantoea stewartii* (refer to International Journal of Systematic Bacteriology, Jan. 1993, 43(1), pp. 162-173).

Examples of the *Enterobacter* bacteria include, but are not limited to, *Enterobacter agglomerans, Enterobacter aerogenes*, and so forth. Specifically, the strains exemplified in European Patent Publication No. 952221 can be used.

A typical strain of the genus *Enterobacter* includes *Enterobacter agglomeranses* ATCC 12287.

Typical strains of the *Pantoea* bacteria include, but are not limited to, *Pantoea ananatis, Pantoea stewartii, Pantoea agglomerans*, and *Pantoea citrea*. Specific examples include the following strains:

*Pantoea ananatis* AJ13355 (FERM BP-6614, European Patent Publication No. 0952221)

*Pantoea ananatis* AJ13356 (FERM BP-6615, European Patent Publication No. 0952221)

*Pantoea ananatis* AJ13601 (FERM BP-7207, European Patent Publication No. 0952221).

Although these strains are described as *Enterobacter agglomerans* in European Patent Publication No. 0952221, they are currently classified as *Pantoea ananatis* on the basis of nucleotide sequence analysis of 16S rRNA etc., as described above.

Examples of the *Erwinia* bacteria include, but are not limited to, *Erwinia amylovora* and *Erwinia carotovora*, and examples of the *Klebsiella* bacteria include *Klebsiella planticola*. Specific examples include the following strains:

*Erwinia amylovora* ATCC 15580

*Erwinia carotovora* ATCC 15713

*Klebsiella planticola* AJ13399 (FERM BP-6600, European Patent Publication No. 955368)

*Klebsiella planticola* AJ13410 (FERM BP-6617, European Patent Publication No. 955368).

The microorganism may be able to cause accumulation of L-glutamic acid in a liquid medium in an amount that exceeds the saturation concentration of L-glutamic acid when cultured under acidic conditions (henceforth also referred to as an L-glutamic acid accumulating ability under acidic conditions). This ability may be acquired via inactivation of the rpoS gene, or may be native to the microorganism. Furthermore, the ability to cause accumulation of L-glutamic acid in an amount that exceeds the saturation concentration can be imparted, particularly by employing a strain which is resistant to L-glumatic acid at a low pH, as described in European Patent Publication No. 1078989.

Specific examples of a microorganism which has a native L-glutamic acid accumulating ability under acidic conditions include, but are not limited to, the *Pantoea ananatis* AJ13356 (FERM BP-6615), AJ13601 (FERM BP-7207) (for these, refer to European Patent Publication No. 0952221), and so forth. *Pantoea ananatis* AJ13356 was deposited at the National Institute of Bioscience and Human-Technology, Agency of Industrial Science and Technology, Ministry of International Trade and Industry (currently, the International Patent Organism Depositary, National Institute of Advanced Industrial Science and Technology, Address: Tsukuba Central 6, 1-1, Higashi 1-Chome, Tsukuba-shi, Ibaraki-ken, 305-8566, Japan) on Feb. 19, 1998, and given an accession number of FERM P-16645. The deposit was then converted to an international deposit under the provisions of Budapest Treaty on Jan. 11, 1999, and given an accession number of FERM BP-6615. The AJ13601 strain was deposited at the National Institute of Bioscience and Human-Technology, Agency of Industrial Science and Technology, Ministry of International Trade and Industry (currently, the International Patent Organism Depositary, National Institute of Advanced Industrial Science and Technology) on Aug. 18, 1999, and given an accession number of FERM P-17516. The deposit was then converted to an international deposit under the provisions of Budapest Treaty on Jul. 6, 2000, and given an accession number of FERM BP-7207.

To impart or enhance the ability to produce L-glutamic acid to bacteria as described above, the bacteria can be modified to enhance the expression of a gene encoding an enzyme involved in L-glutamic acid biosynthesis.

Enzymes that are involved in L-glutamic acid biosynthesis include glutamate dehydrogenase (hereinafter, also referred to as "GDH"), glutamine synthetase, glutamate synthase, isocitrate dehydrogenase, aconitate hydratase, citrate synthase (hereafter, also referred to as "CS"), methylcitrate synthase (hereafter, also referred to as "PRPC", phosphoenolpyruvate carboxylase (hereafter, also referred to as "PEPC"), pyruvate dehydrogenase, pyruvate kinase, enolase, phosphoglyceromutase, phosphoglycerate kinase, glyceraldehyde-3-phosphate dehydrogenase, triosephosphate isomerase, fructose bisphosphate aldolase, phosphofructokinase, glucose phosphate isomerase, and so forth. Among these enzymes, one or more of CS or PRPC, PEPC, and GDH are preferred. Three of these are more preferred.

Hereinafter, methods for modifying bacteria to enhance expression of an objective gene will be explained.

The first method is by increasing the copy number of the objective gene. For example, the objective gene can be cloned into an appropriate plasmid, and the plasmid used to transform a host bacterium. For example, when the gene encoding CS (gltA), the gene encoding PRPC (prpC), the gene encoding PEPC (ppc), or the gene encoding GDH (gdhA) is the objective gene, the nucleotide sequences of these genes from *Escherichia* bacteria and *Corynebacterium* bacteria have been reported (Biochemistry, vol. 22, pp. 5243-5249, 1983; J. Biochem., vol. 95, pp. 909-916, 1984; Gene, vol. 27, pp. 193-199, 1984; Microbiology, vol. 140, pp. 1817-1828, 1994; Mol. Gen. Genet., vol. 218, pp. 330-339, 1989; Molecular Microbiology, vol. 6, pp. 317-326, 1992); and therefore, these genes can be obtained by synthesizing primers based on their respective nucleotide sequences, and performing PCR using the chromosomal DNA of bacteria belonging to the family Enterobacteriaceae as the template.

Examples of the plasmid which can be transformed include plasmids which are autonomously replicable in bacteria belonging to family Enterobacteriaceae, for example, pUC19, pUC18, pBR322, RSF1010, pHSG299, pHSG298, pHSG399, pHSG398, pSTV28, pSTV29 (pHSG and pSTV can be obtained from Takara Bio), pMW119, pMW118, pMW219, pMW218 (plasmids of pMW series can be obtained from Nippon Gene), and so forth. Phage DNA may also be used as a vector, instead of a plasmid. Examples of plasmids which can be used to simultaneously enhance the activities of CS or PRPC, PEPC, and GDH include RSFCPG which contains the gltA, ppc, and gdhA genes (refer to European Patent Publication No. 0952221), and RSFPPG which is obtained by replacing the gltA gene in RSFCPG with the prpC gene (refer to the examples).

Examples of the transformation method include treating recipient cells with calcium chloride so as to increase the permeability of DNA, which has been reported for *Escherichia coli* K-12 (Mandel, M. and Higa, A., J. Mol. Biol., 53, 159 (1970)), preparing competent cells from cells which are at the growth phase followed by introducing the DNA thereinto, which has been reported for *Bacillus subtilis* (Duncan, C. H., Wilson, G. A. and Young, F. E., Gene, 1, 153 (1977)), and so forth. In addition to these methods, making the DNA-recipient bacterial cells into protoplasts or spheroplasts which can easily take up recombinant DNA, followed by introducing the recombinant DNA into the DNA-recipient cells is an alternative method, and which is known to be applicable to *Bacillus subtilis*, actinomycetes, and yeasts (Chang, S. and Choen, S. N., Molec. Gen. Genet., 168, 111 (1979); Bibb, M. J., Ward, J. M. and Hopwood, O. A., Nature, 274, 398 (1978); Hinnen, A., Hicks, J. B. and Fink, G. R., Proc. Natl. Sci., USA, 75, 1929 (1978)). In addition, transformation of microorganisms can also be performed by the electric pulse method (Japanese Patent Laid-open No. 2-207791).

Increasing the copy number of an objective gene can also be achieved by introducing multiple copies of the gene into the chromosomal DNA of a microorganism. In order to introduce multiple copies of a gene into the chromosomal DNA of a microorganism, homologous recombination (Experiments in Molecular Genetics, Cold Spring Harbor Lab. (1972)) can be carried out by targeting a sequence which exists in multiple copies on the chromosomal DNA. Sequences which exist in multiple copies on the chromosomal DNA include repetitive DNA and inverted repeats which are present at the end of a transposable element. Alternatively, as disclosed in Japanese Patent Laid-open No. 2-109985, it is also possible to incorporate an objective gene into a transposon, and transfer it, resulting in the introduction of multiple copies of the gene to the chromosomal DNA. Furthermore, the objective gene can also be incorporated into a host chromosome using Mu phage (Japanese Patent Laid-open No. 2-109985)

The second method is by enhancing expression of an objective gene by replacing an expression control sequence of the objective gene, such as a promoter on the chromosomal DNA or plasmid, with a stronger one. For example, the lac promoter, trp promoter, trc promoter, PR promoter, lacUV promoter, and so forth are all known as strong promoters. Moreover, it is also possible to substitute several nucleotides in a promoter region of a gene, so that the promoter is strengthened, as disclosed in International Patent Publication WO00/18935. Substitution of the expression control sequence can be performed, for example, in the same manner as in gene substitution using a temperature-sensitive plasmid. An example of a vector having a temperature-sensitive replication origin effective in bacteria belonging to the family Enterobacteriaceae is the plasmid pMAN997, described in International Patent Publication WO99/03988, and so forth. Furthermore, gene-substituted strains can be easily selected by using quinaldic acid, which is described later.

Modifying an expression control sequence can be done in conjunction with increasing the copy number of gene, as described above.

Examples of microorganisms which have been modified by the method described above so that expression of citrate synthase gene, methyl citrate synthase gene, phosphoenolpyruvate carboxylase gene and/or glutamate dehydrogenase gene is enhanced include the microorganisms disclosed in European patent publication Nos. EP1078989, 0955368, 0952221, and 1078989, Japanese Patent Laid-open No. 2006-129840, International Patent Publication No 2006/051660, and so forth.

Furthermore, the ability to produce L-glutamic acid can also be imparted by enhancing the 6-phosphogluconate dehydratase activity, 2-keto-3-deoxy-6-phosphogluconate aldolase activity, or both. Examples of a microorganism with increased activities of 6-phosphogluconate dehydratase activity and 2-keto-3-deoxy-6-phosphogluconate aldolase include the microorganism disclosed in European patent publication EP1352966.

L-glutamic acid producing ability may be imparted by reducing or eliminating the activity of an enzyme that catalyzes a branch reaction of the L-glutamic acid biosynthesis pathway, and results in producing a compound other than L-glutamic acid. Examples of such an enzyme include 2-oxoglutarate dehydrogenase, isocitrate lyase, phosphate acetyltransferase, acetate kinase, acetohydroxy acid synthase, acetolactate synthase, formate acetyltransferase, lactate dehydrogenase, glutamate decarboxylase, 1-pyrroline-5-carboxylate dehydrogenase, and so forth. It is particularly preferable to reduce or eliminate the activity of 2-oxoglutarate dehydrogenase.

In order to reduce or eliminate the activities of the aforementioned enzymes, mutations can be introduced into the genes of the aforementioned enzymes by typical mutagenesis or genetic engineering techniques. Mutagenesis treatments include, for example, irradiation with X-rays or ultraviolet rays, or treatment with a mutagenesis agent such as N-methyl-N'-nitro-N-nitrosoguanidine, and so forth. The mutation may be introduced into the coding region of the gene encoding the enzyme protein, or into a region responsible for regulating expression, such as a promoter. Genetic engineering techniques include genetic recombination, transduction, cell fusion, and so forth.

A decrease in the intracellular activity of the objective enzyme, and the degree thereof, can be confirmed by measuring the enzyme activity in a cell extract or a purified fraction thereof obtained from the candidate strain, and comparing it with that of a wild-type strain. For example, 2-oxoglutarate dehydrogenase activity can be measured by the method of Reed et al. (Reed L. J. and Mukherjee B. B., Methods in Enzymology, 13, pp. 55-61 (1969)).

Specifically, examples of bacterium with decreased or eliminated activity of 2-oxoglutarate dehydrogenase include the following:

*Pantoea ananatis* AJ13601 (FERM BP-7207, EP1078989A)

*Pantoea ananatis* AJ13356 (FERM BP-7207, U.S. Pat. No. 6,331,419)

*Pantoea ananatis* SC17sucA (FERM BP-8646, WO2005/085419)

*Klebsiella planticola* AJ13410 strain (FERM BP-6617, U.S. Pat. No. 6,197,559).

The SC17sucA strain was obtained from SC17 strain by disrupting 2-oxoglutarate dehydrogenase gene. The SC17 strain was obtained by selecting a low-phlegm production mutant strain from AJ13355. AJ13355 strain was isolated from nature due to its ability to proliferate in a medium containing L-glutamic acid and a carbon source at low pH condition. The AJ13601 strain was obtained by introduction into the SC17sucA strain the gltA, ppc, and gdhA genes derived from *Escherichia coli* and the gltA gene derived from *Brevibacterium lactofermentum*. Then, a high concentration L-glutamic acid-resistant strain at low pH was selected, and the strain having a high proliferation degree and a high L-glutamic acid producing ability was finally selected. The SC17sucA strain was assigned a private number of AJ417, and it was deposited at the National Institute of Bioscience and Human-Technology, Agency of Industrial Science and Technology, Ministry of Economy, Trade and Industry (currently, the International Patent Organism Depositary, National Institute of Advanced Industrial Science and Technology, Tsukuba Central 6, 1-1, Higashi 1-Chome, Tsukuba-shi, Ibaraki-ken, 305-8566) on Feb. 26, 2004 and given an accession number of FERM BP-08646.

The bacterium has the aforementioned ability to produce L-glutamic acid, belongs to the genus *Pantoea, Enterobacter, Klebsiella* or *Erwinia*, and has been modified to inactivate the rpoS gene by gene recombination.

The bacterium can be obtained by modifying a bacterium having an ability to produce L-glutamic acid and belonging to the genus *Pantoea, Enterobacter, Klebsiella* or *Erwinia*, so that the rpoS gene is inactivated by gene recombination. In the breeding of the bacterium belonging to the genus *Pantoea, Enterobacter, Klebsiella* or *Erwinia*, either imparting the ability to produce L-glutamic acid or inactivating the rpoS gene may be performed first.

The phrase "bacterium has been modified to inactivate the rpoS gene" means that the bacterium has been modified so that the RpoS protein does not function normally as compared with that in an unmodified strain, such as a parent strain or a wild-type strain. The results of the modification of the rpoS gene by gene recombination include, for example, a decrease in the number of RpoS molecules per cell as compared with that of the parent strain or a wild-type strain, no production of the RpoS protein, reduction of the activity of the RpoS protein per molecule, or the disappearance of the activity, and so forth. The number of RpoS molecules can be decreased by reducing the expression of the rpoS gene. The decrease in expression of the rpoS gene includes either a decrease in the transcription or translation of the rpoS mRNA. Moreover, eliminating production of the RpoS protein, reduction of the activity of the RpoS protein per molecule, or elimination of the activity can be attained by disrupting the rpoS gene. Examples of the wild-type strain which can be used for comparison include the *Pantoea ananatis* AJ13355 strain, the *Klebsiella planticola* AJ13399 strain, and so forth.

Specifically, the rpoS gene can be modified by deleting a part or the entire coding region of the rpoS gene on the chromosome, modifying an expression control sequence, such as promoters or a Shine-Dargarno (SD) sequence, or the like. Furthermore, the expression of the gene can also be reduced by modifying an untranslated region, other than the expression control sequences. Furthermore, the entire rpoS gene, including the sequences upstream and downstream of the rpoS gene on the chromosome, may be deleted. Moreover, amino acid substitutions (missense mutation), a stop codon (nonsense mutation), or a frameshift mutation resulting in adding or deleting one or two nucleotides may be introduced into the region encoding rpoS on the chromosome (Journal of Biological Chemistry, 272: 8611-8617 (1997); Proceedings of the National Academy of Sciences, USA 95 5511-5515 (1998); Journal of Biological Chemistry, 266, 20833-20839 (1991)).

The phrase "modified by gene recombination" means a deletion of a part or the entire expression control sequence, such as promoter region, or a deletion of a coding region or non-coding region of the rpoS gene on the chromosome. It may also mean insertion of other sequences into the foregoing regions using homologous recombination to reduce the intracellular rpoS activity, but not modified by usual mutagenesis using X-ray or ultraviolet irradiation or a mutagen such as N-methyl-N'-nitro-N-nitrosoguanidine. The rpoS gene is preferably inactivated by modification of the rpoS gene to such a degree that the function of the rpoS gene is not restored by a spontaneous mutation.

When modifying an expression control sequence, preferably one or more nucleotides is/are altered, more preferably two or more nucleotides are altered, particularly preferably three or more nucleotides are altered. When deleting within the coding region, the region to be deleted may include the N-terminus, an internal region, the C-terminus, or the entire coding region, so long as the function of the RpoS protein is reduced or eliminated. In general, deleting longer regions more reliably results in the inactivation of the rpoS gene. Moreover, it is preferred that the reading frames upstream and downstream of the deleted region do not conform to each other.

When inserting a sequence into the coding region, the insertion point may be within any region in the rpoS gene. Inserting a longer region more reliably results in the inactivation of the rpoS gene. It is preferred that the reading frames upstream and downstream of the insertion site do not conform to each other. The sequence to be inserted is not particularly limited so long as it reduces or eliminates the function of the RpoS protein, and examples include, for example, antibiotic resistance genes and transposons carrying a gene useful for L-glutamic acid production.

The rpoS gene on the chromosome can be modified as described above by, for example, preparing a deletion-type rpoS gene by deleting a partial sequence of the rpoS gene, transforming a bacterium with a DNA containing the deletion-type gene resulting in homologous recombination of the gene and the rpoS gene on the chromosome, and thereby substituting the deletion-type gene for the rpoS gene on the chromosome. Even if a protein is produced from the deletion-type rpoS gene, its three-dimensional structure will be different from that of the wild-type RpoS protein, and thus the function thereof will be reduced or eliminated. Gene disruption resulting from gene substitution using homologous recombination as described above has been already reported, and examples thereof include using a plasmid containing a temperature-sensitive replication origin, or a plasmid capable of conjugational transfer, utilizing a suicide vector which does not have a replication origin able to function in the chosen host, and so forth (U.S. Pat. No. 6,303,383 or Japanese Patent Laid-open No. 05-007491).

Moreover, the rpoS gene can also be inactivated via gene disruption using quinaldic acid, resulting in a double crossover recombinant strain.

Quinaldic acid is an analogue of tetracycline, and is excreted out of cells by a tetracycline-excreting protein encoded by Tn10. Quinaldic acid is a weakly acidic substance, and it loses its electric charge and takes an electorically free form under weakly acidic conditions. Therefore, it can easily pass through cell membranes. Under weakly acidic conditions, quinaldic acid is excreted by the tetracycline excretion system and then, the excreted quinaldic acid converts to the free form in the weakly acidic environment out of the cell, and flows into the cell again, and, as a result, the proton concentration gradient between the outside and inside of the cell disappears. That is, a strain containing the tetracycline excreting gene (tetracycline resistance gene) derived from Tn10 becomes sensitive to quinaldic acid under weakly acidic conditions (J. Bacteriol., August 1980, 143(2), p. 926-33). If the tetracycline resistance gene (Tn10) is carried on a vector, which is incorporated into the chromosome by single crossover, the strain can be dominantly selected with tetracycline, and a strain in which the vector moiety is eliminated by double crossover can be dominantly selected in a medium containing quinaldic acid. Thus, the operation becomes simple.

Therefore, when the tetracycline resistance gene is inserted into the vector for gene recombination, isolating a double recombinant strain without using a marker gene is simple.

The decrease in transcription of the rpoS gene can be confirmed by comparing the amount of rpoS mRNA with that of a wild-type strain or an unmodified strain. The amount of mRNA can be evaluated by Northern hybridization, RT-PCR, and so forth (Molecular Cloning, Cold spring Harbor Laboratory Press, Cold spring Harbor (USA), 2001). Although the decrease in transcription may be to any degree, so long as transcription is decreased as compared with that of a wild-type strain or an unmodified strain, it is desirably decreased to, for example, at least 75% or less, 50% or less, 25% or less, or 10% or less of the transcription in a wild-type strain or an unmodified strain, and it is particularly preferred that the rpoS gene is not expressed at all.

The decrease of the amount of the protein encoded by the rpoS gene can be confirmed by Western blotting using antibodies (Molecular cloning, Cold spring Harbor Laboratory Press, Cold spring Harbor (USA), 2001). Although the decrease of the amount of the protein may be of any degree so long as the amount is decreased compared with that of a wild-type strain or an unmodified strain, it is desirably decreased by, for example, at least 75% or less, 50% or less, 25% or less, or 10% or less of the amount in a wild-type strain or an unmodified strain, and it is particularly preferred that the protein is not produced at all (activity has completely disappeared).

The protein encoded by the rpoS gene, i.e., the RpoS protein, is the sigma S factor of RNA polymerase. RNA polymerase consists of α, β, β', and sigma (σ) subunits. The sigma factor binds to the core enzyme which includes the α, β0 and β' subunits, and recognizes the promoter for the gene transcribed by the RNA polymerase. The "function of the RpoS protein" refers the recognition of the promoter of the gene transcribed by the RNA polymerase. If the RpoS does not function normally, expression of genes which are expressed when the RpoS functions normally, such as a wild-type strain, is reduced or eliminated. Reducing RpoS function in cells can be confirmed by detecting expression of a gene which is typically transcribed by rpoS, such as the bolA gene, by Northern hybridization or the RT-PCR method (J. Bacteriol., 1991 July, 173 (14): 4474-81).

Examples of the RpoS protein from Enterobacteriaceae include the protein of SEQ ID NO: 2. This protein is encoded by the rpoS gene from *Pantoea ananatis* (SEQ ID NO: 1). Furthermore, since the nucleotide sequence of the rpoS gene may vary depending on the species or strain of bacteria belonging to the family Enterobacteriaceae, the rpoS gene may be a variant of the nucleotide sequence of SEQ ID NO: 1. Variants of the rpoS gene can be found by using the nucleotide sequence of SEQ ID NO: 1 in a BLAST search (blast.genome.jp/), or the like. Furthermore, variants of the rpoS gene include a gene that can be amplified by PCR using a rpoS gene homologue, such as the chromosome from an Enterobacteriaceae bacterium as a template, and synthetic oligonucleotides such as those of SEQ ID NOS: 7 and 10 as primers.

An example of the RpoS protein is the protein having the amino acid sequence of SEQ ID NO: 2. Furthermore, because differences may exist in codon usage and the nucleotide sequences of the rpoS gene depending on the species or strains of bacteria, the gene may encode the amino acid sequence of SEQ ID NO: 2, but which includes substitutions, deletions, insertions, or additions of one or several amino acid residues so long as the function of the RpoS protein is maintained. The number of these amino acid differences may be, for example, 1 to 20, preferably 1 to 10, more preferably 1 to 5. These differences are typically conservative mutations that allow normal production of the RpoS protein. A conservative mutation is a mutation wherein substitution takes place mutually among Phe, Trp, Tyr, if the substitution site is an aromatic amino acid; among Leu, Ile, Val, if the substitution site is a hydrophobic amino acid; between Gln, Asn, if it is a polar amino acid; among Lys, Arg, His, if it is a basic amino acid; between Asp, Glu, if it is an acidic amino acid; and between Ser, Thr, if it is an amino acid having a hydroxyl group. Typical conservative mutations are conservative substitutions. Specific examples of substitutions that are considered to be conservative include: substitution of Ser or Thr for Ala, substitution of Gln, His or Lys for Arg, substitution of Glu, Gln, Lys, His or Asp for Asn, substitution of Asn, Glu or Gln for Asp, substitution of Ser or Ala for Cys, substitution of Asn, Glu, Lys, His, Asp or Arg for Gln, substitution of Asn, Gln, Lys or Asp for Glu, substitution of Pro for Gly, substitution of Asn, Lys, Gln, Arg or Tyr for His, substitution of Leu, Met, Val or Phe for Ile, substitution of Ile, Met, Val or Phe for Leu, substitution of Asn, Glu, Gln, His or Arg for Lys, substitution of Ile, Leu, Val or Phe for Met, substitution of Trp, Tyr, Met, Ile or Leu for Phe, substitution of Thr or Ala for Ser, substitution of Ser or Ala for Thr, substitution of Phe or Tyr for Trp, substitution of His, Phe or Trp for Tyr, and substitution of Met, Ile or Leu for Val.

Moreover, in addition to the gene having the nucleotide sequence of SEQ ID NO: 1, the rpoS gene may be a variant which hybridizes with the nucleotide sequence shown in SEQ ID NO: 1, or a probe which can be prepared from the nucleotide sequence under stringent conditions. "Stringent conditions" include those under which a specific hybrid, for example, a hybrid having homology of not less than 80%, preferably not less than 90%, more preferably not less than 95%, and still more preferably not less than 97%, and most preferably not less than 99% is formed and a hybrid having homology lower than the above is not formed. Alternatively, stringent conditions are exemplified by washing one time, preferably two or three times at a salt concentration corresponding to 60° C., 1×SSC, 0.1% SDS, preferably 60° C., 0.1×SSC, 0.1% SDS at 60° C., more preferably 68° C., 0.1× SSC, 0.1% SDS conducted one, two, or three times. The length of the probe may be suitably selected depending on the hybridization conditions, and is usually 100 bp to 1 kbp.

<2> Improvement of the Growth of a Microorganism Able to Produce L-Glutamic Acid Under Acidic Conditions L-glutamic acid productivity of a microorganism can be improved by inactivating the rpoS gene in the microorganism by gene recombination as described above. Specifically, the growth of the microorganism under acidic conditions can be improved. Acidic conditions are indicated by, for example, a pH of 3 to 5, more preferably a pH of 4 to 5.

Examples of the microorganism include bacteria belonging to the genus *Pantoea, Enterobacter, Serratia, Klebsiella*, or *Erwinia*.

Specifically, the microorganism is preferably cultured under acidic conditions, which results in production and accumulation of L-glutamic acid accompanied with precipitation of L-glutamic acid.

When the microorganism is able to accumulate L-glutamic acid under acidic conditions, in particular, production of L-glutamic acid can be improved by improving the growth of the microorganism under acidic conditions.

<3> Method for Producing L-Glutamic Acid

L-glutamic acid can be produced by culturing the bacterium in a medium to produce and cause accumulation of L-glutamic acid in the medium, and collecting L-glutamic acid from the medium.

The chosen culture medium may be a typical medium containing a carbon source, nitrogen source, and inorganic salts as well as trace amounts of organic nutrients as required, such as amino acids and vitamins. Either a synthetic or natural medium may be used. The carbon and nitrogen sources used in the medium may be of any type so long as the chosen substances can be utilized by the chosen strain.

As the carbon source, saccharides such as glucose, glycerol, fructose, sucrose, maltose, mannose, galactose, starch hydrolysate, and molasses can be used. In addition, organic acids, such as acetic acid and citric acid, or alcohols, such as ethanol, may be used alone or in combination with other carbon sources. As the nitrogen source, ammonia, ammonium salts such as ammonium sulfate, ammonium carbonate, ammonium chloride, ammonium phosphate, and ammonium acetate, nitrates, and so forth can be used. As the organic nutrients, amino acids, vitamins, fatty acids, nucleic acids, and compounds containing these substances such as peptone, casamino acids, yeast extract, and soybean protein hydrolysate can be used. When an auxotrophic mutant strain that requires an amino acid, or the like, for growth is used, the required nutrient is preferably supplemented. As mineral salts, phosphates, magnesium salts, calcium salts, iron salts, manganese salts, and so forth can be used.

The culture is preferably performed with aeration, while the fermentation temperature is preferably controlled to be 20 to 45° C., and the pH to be 3 to 9. When the pH falls during the culture, the medium is neutralized by the addition of, for example, calcium carbonate or an alkali, such as ammonia gas. A substantial amount of L-glutamic acid is produced in the culture broth after 10 to 120 hours of culture under such conditions as described above.

Moreover, L-glutamic acid can be precipitated during the culture into the medium by using a liquid medium which is adjusted so that L-glutamic acid precipitates. L-glutamic acid precipitates, for example, at a pH of 5.0 to 4.0, preferably a pH of 4.5 to 4.0, more preferably a pH of 4.3 to 4.0, particularly preferably pH 4.0. In order to improve bacterial growth under acidic conditions, as well as allow for efficient precipitation of L-glutamic acid, it is desirable that the pH is preferably 5.0 to 4.0, more preferably 4.5 to 4.0, more preferably 4.3 to 4.0. The culture may be performed at a pH within the aforementioned ranges for part or the total period of the culture.

After completion of the culture, L-glutamic acid can be collected from the culture broth by known methods. For example, after the cells are removed from the culture broth, L-glutamic acid can be collected by concentration-crystallization, ion exchange chromatography, or the like. When the culture is performed under conditions favorable for precipitating L-glutamic acid in the medium, the L-glutamic acid which precipitates into the medium can be collected by centrifugation, filtration, or the like. In this case, it is also possible to crystallize any L-glutamic acid which has dissolved in the medium, and then collect the crystallized L-glutamic acid together with the L-glutamic acid which has already precipitated.

EXAMPLES

The present invention will be explained more specifically below with reference to the following non-limiting Examples.

<1> Preparation of rpoS Gene-Disrupted Strain (1) Construction of the Plasmid pUT-Tn10 for Gene Disruption To disrupt the rpoS gene, a vector having the tetracycline resistance gene for use in gene disruption using quinaldic acid and tetracycline resistance gene was constructed. First, the tetracycline resistance gene from Tn10 was inserted into the vector. The tetracycline resistance gene was amplified by PCR using primers Tn10-750Xho (SEQ ID NO: 3) and Tn10-3020Xho (SEQ ID NO: 4) and the chromosome from the *Escherichia coli* K-12 ME8424 strain (Hfr, P045, thi, relA1, tyrA::Tn10, ung-1, and nadB, provided by the National Institute of Genetics, Japan) as a template. Moreover, PCR was performed using primers pUT-3710Xho (SEQ ID NO: 5) and pUT-3020Xho (SEQ ID NO: 6) and pUT399 as a template. This resulted in a fragment of pUT399 with the XhoI site. Both amplified fragments were treated with XhoI, and then ligated to obtain the plasmid pUT-Tn10. pUT399 has a replication origin of R6K and contains the mob region required for conjugational transfer, and it cannot be replicated in a bacterial strain which does not have the pir gene (available from Biomedal, refer to R. Simon., et al., BIO/TECHNOLOGY NOVEMBER 1983, 784-791 (1983)).

(2) Preparation of rpoS Gene-Disrupted Strain

PCR was performed by using the chromosome of the *Pantoea ananatis* SC17sucA strain (FERM BP-8646) as a template and primers rpoS-F1 (SEQ ID NO: 7)/rpoS-FR (SEQ ID NO: 8), or rpoS-RF (SEQ ID NO: 9)/rpoS-R1 (SEQ ID NO: 10). As a result, about 2.1 kb both to the upstream and downstream of the rpoS gene was amplified. Then, these amplified fragments were used as templates with the combination of primers KpnI-rpoS-F2 (SEQ ID NO: 11)/KpnI-rpoS-R2 (SEQ ID NO: 12) to amplify an about 4.1 kb fragment, and this fragment was cloned into pGEM-T Easy (Promega).

The resulting plasmid was treated with KpnI, and the fragment (about 4.1 kb) was ligated to the KpnI site of pUT-Tn10 to obtain pUT-Tn10/ΔrpoS. This plasmid was introduced into the *Escherichia coli* S17-1λ-pir strain having λ-pir (available from Biomedal, R. Simon, et al., BIO/TECHNOLOGY NOVEMBER 1983, 784-791 (1983)), and this plasmid was transferred from the resulting strain into the SC17sucA strain by conjugation.

By selection in M9 minimal medium (5 g of glucose, 2 mM magnesium sulfate, 3 g of monopotassium phosphate, 0.5 g of sodium chloride, 1 g of ammonium chloride and 6 g of disodium phosphate in 1 L of pure water) containing 25 mg/L of chloramphenicol, 100 mg/L of L-lysine, 100 mg/L of L-methionine, 100 mg/L of diaminopimelic acid, and 5 g/L of sucrose, the SC17sucA strain (FERM BP-8646) with pUT-Tn10/ΔrpoS incorporated into the rpoS gene site on the chromosome was obtained.

This strain was purified on L medium (10 g of Bacto tryptone, 5 g of yeast extract, 5 g of NaCl and 15 g of agar in 1 L of pure water, pH 7.0) also containing components of minimal medium (0.5 g of glucose, 2 mM magnesium sulfate, 3 g of monopotassium phosphate, 0.5 g of sodium chloride, 1 g of ammonium chloride and 6 g of disodium phosphate in 1 L of pure water), 25 mg/L of chloramphenicol, and 12.5 mg/L of tetracycline. The cells were also cultured on the same medium, but without the antibiotics. Several colonies were picked up, and cultured overnight in a liquid medium having the same composition. The culture was diluted 100 to 10,000 times with sterilized water, and applied to a quinaldic acid plate (medium obtained by dissolving 5 g of Bacto tryptone, 5 g of yeast extract, 40 g of NaCl, 0.05 g of tetracycline and 10 g of $NaH_2PO_4$ in 900 mL of purified water, adjusting the solution to pH 5.2 with KOH, mixing 20 g of agar with the solution, autoclaving the mixture at 120° C. for 20 minutes, and adding 0.2 g of quinaldic acid, 13.6 mg of $ZnCl_2$ and 5 g of glucose dissolved in 100 mL of purified water and subjected to filter sterilization to the autoclaved mixture). The structure of the rpoS gene in the colonies which appeared was confirmed by PCR using primers. The strain having the disrupted rpoS gene was designated SC17sucArpoS.

The plasmid RSFPPG was constructed. This plasmid contains the L-glutamic acid biosynthesis genes, including prpC (International Patent Publication WO2006/051660), ppc, and gdh (European Patent Publication No. 0999282).

Primer 1 (SEQ ID NO: 13) and primer 2 (SEQ ID NO: 14) were designed to amplify a moiety of RSFCPG (European Patent Publication No. 1233068) other than the ORF of the gltA gene. By using these primers and RSFCPG as a template, PCR was performed to obtain a fragment of about 14.9 kb. As for prpC, PCR was performed by using primer 3 (SEQ ID NO: 15) and primer 4 (SEQ ID NO: 16), and the chromosomal DNA of the E. coli W3110 strain as a template to obtain a fragment of about 1.2 kb. Both of these PCR products were treated with BglII and KpnI, ligated, and then used to transform the E. coli JM109 strain. All the colonies which appeared were collected, and plasmids were extracted from the colonies as a mixture. The CS deficient strain of E. coli, ME8330, was transformed with the plasmid mixture, and the cell suspension was applied to the M9 minimal medium (5 g of glucose, 2 mM magnesium sulfate, 3 g of monopotassium phosphate, 0.5 g of sodium chloride, 1 g of ammonium chloride and 6 g of disodium phosphate in 1 L of pure water) containing 50 mg/L of uracil and 5 mg/L of thiamine HCl. From the colonies which appeared, a plasmid was extracted and designated RSFPPG. The Glu production plasmid RSFPPG was introduced into the SC17sucArpoS strain to construct a rpoS-deficient Glu-producing bacterium, SC17sucArpoS/RSFPPG.

<2> Growth of the rpoS Gene-Disrupted Strain Under Acidic Conditions

Figure 2:
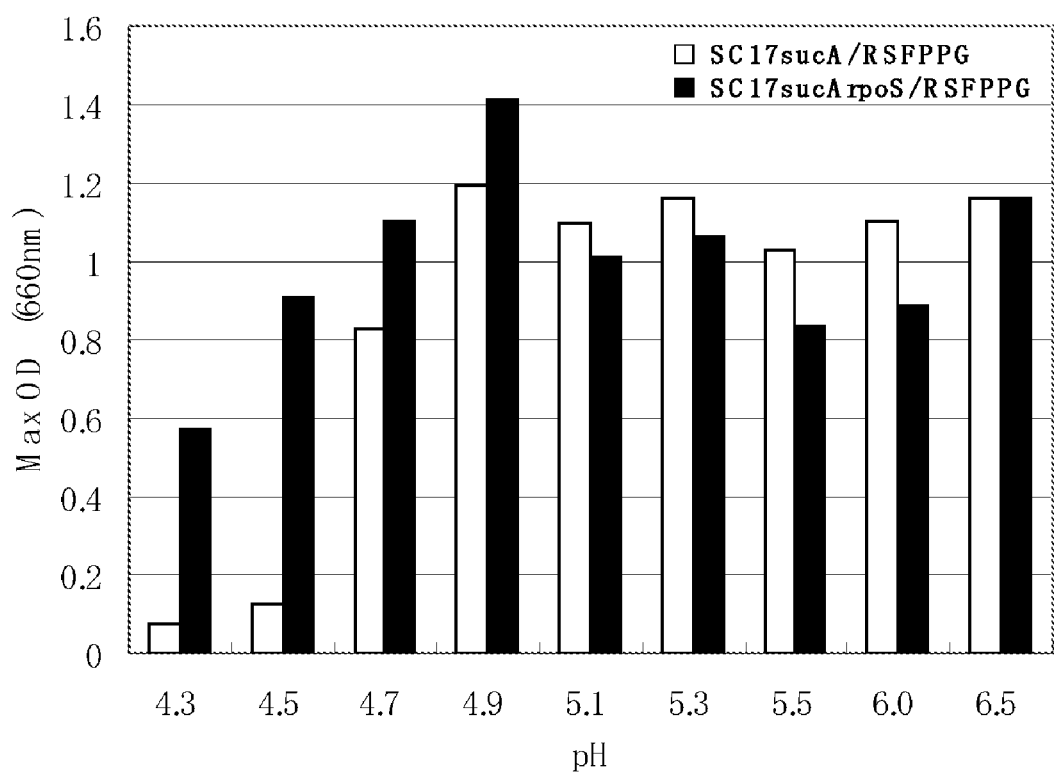
FIG. 2 shows the OD attained by the rpoS-deficient strain under acidic conditions.

Growth of SC17sucArpoS/RSFPPG was investigated under various pH conditions. The SC17sucArpoS/RSFPPG strain and the SC17sucA/RSFPCPG strain (rpoS wild-type) were cultured overnight on a solid medium, which was prepared by adding ingredients of minimal medium to the L medium, and the cells were washed twice with sterilized water. The cells were inoculated into 5 mL of the minimal medium (5 g of glucose, 2 mM magnesium sulfate, 3 g of monopotassium phosphate, 0.5 g of sodium chloride, 1 g of ammonium chloride, 6 g of disodium phosphate, 100 mg of lysine hydrochloride, 100 mg of L-methionine and 100 mg of diaminopimelic acid, and 30 g of L-glutamic acid in 1 L of purified water, adjusted to various pH levels with ammonia) at OD660 nm of 0.05, and OD was measured over time by using the automatic OD measuring apparatus TN1506, produced by ADVANTEC. The results are shown in FIGS. 1 and 2.

At pH 5.1 or higher, there was no difference between the SC17sucA/RSFPPG control strain and the SC17sucArpoS/RSFPPG strain. However, when the pH was 4.9 or lower, the rpoS gene-disrupted strain tended to show more favorable growth. Moreover, this effect tended to become more significant as the pH of the medium was lowered. Therefore, disruption of the rpoS gene was effective to improve growth under acidic conditions.

<3> Production of L-Glutamic Acid by the rpoS Gene-Disrupted Strain Under Acidic Conditions Then, the ability of the SC17sucArpoS/RSFPPG strain to produce L-glutamic acid was evaluated under acidic conditions.

The SC17sucA/RSFPPG strain and the SC17sucArpoS/RSFPPG strain were cultured overnight in a medium, which was prepared by adding ingredients of minimal medium (5 g of glucose, 2 mM magnesium sulfate, 3 g of monopotassium phosphate, 0.5 g of sodium chloride, 1 g of ammonium chloride and 6 g of disodium phosphate in 1 L of pure water) and 12.5 mg/L of tetracycline to the L medium (10 g of Bacto tryptone, 5 g of yeast extract, 5 g of NaCl and 15 g of agar in 1 L of pure water, pH 7.0). The cells were grown on each plate, and then were each inoculated into 300 mL culture media (listed below) in jar fermentors and cultured with aeration of 1/1 vvm at 34° C. and pH 4.7 adjusted with ammonia gas. When the sugar was depleted, additional sugar was added to continue the culture. As for the SC17sucArpoS/RSFPPG strain, when the L-glutamic acid concentration reached the saturation solubility, pectin was added at a concentration of 1 g/L.

Compositions of media (all the concentrations are final concentrations):

group A: 100 g/L of sucrose, 1.2 g/L of $MgSO_4.7H_2O$, 0.2 mL/L of GD113 (antifoaming agent)

group B: 5 g/L of $(NH_4)_2SO_4$, 6 g/L of $KH_2PO_4$, 6 g/L of yeast extract (Difco), 1.5 g/L of NaCl, 60 mg/L of $MnSO_4.5H_2O$, 0.8 g/L of L-lysine, 0.6 g/L of DL-methionine, 0.6 g/L of DL-diaminopimelic acid, 4 g/L of betaine group C: 60 mg/L of $FeSO_4.7H_2O$ For each group, the ingredients were sterilized at 120° C. for 20 minutes, then mixed and dispensed in a volume of 300 mL each into 1 L-volume jar fermentors.

Figure 3:
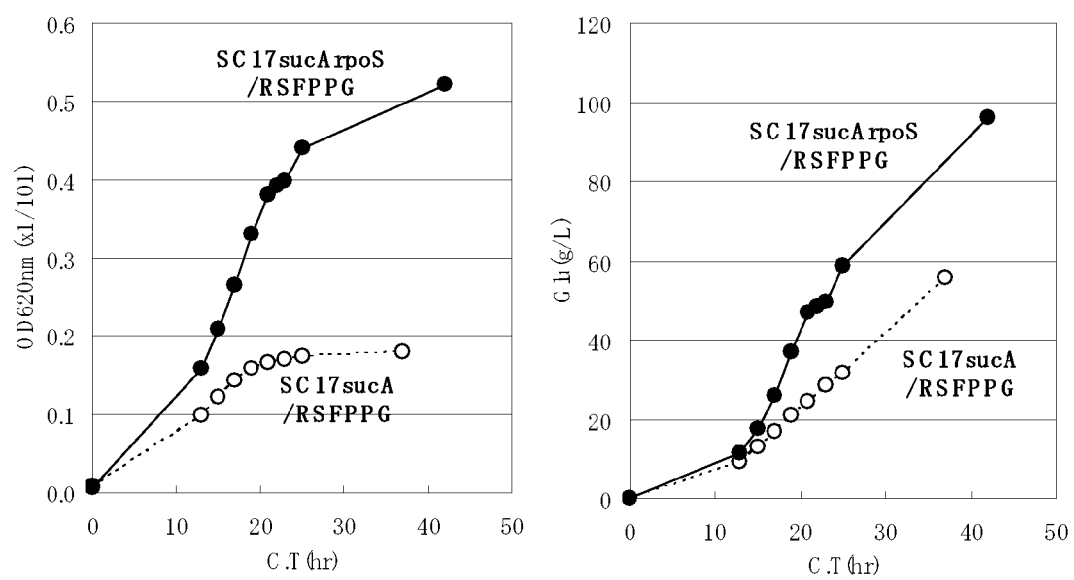
FIG. 3 shows the amount of L-glutamic acid produced by the rpoS-deficient strain under acidic conditions.

Feed medium: 700 g/L of sucrose, 0.2 mL/L of GD113, sterilized at 120° C. for 20 minutes The results for each of the aforementioned cultures are shown in FIG. 3. The SC17sucA/RSFPPG control strain tended to stop growing in the middle of the culture. On the other hand, growth of the SC17sucArpoS/RSFPPG strain did not stop, and this strain showed L-glutamic acid accumulation markedly exceeding that obtained with SC17sucA/RSFPPG.

INDUSTRIAL APPLICABILITY

By using the microorganism of the present invention, L-glutamic acid can be efficiently produced by fermentation. Moreover, by inactivating the rpoS gene, growth of L-glutamic acid producing bacteria under acidic conditions can be improved.

While the invention has been described in detail with reference to preferred embodiments thereof, it will be apparent to one skilled in the art that various changes can be made, and equivalents employed, without departing from the scope of the invention. Each of the aforementioned documents is incorporated by reference herein in its entirety.

We claim:

1. A method for producing L-glutamic acid comprising:
   A) culturing in a medium an L-glutamic acid-producing bacterium which belongs to a genus of bacteria selected from the group consisting of *Pantoea, Enterobacter, Klebsiella*, and *Erwinia*, and
   B) collecting L-glutamic acid from the medium,
   wherein the bacterium has been modified by gene recombination so that the rpoS gene is inactivated;
   wherein the rpoS gene encodes a protein selected from the group consisting of:
   (A) the protein comprising the amino acid sequence of SEQ ID NO: 2, and
   (B) the protein comprising the amino acid sequence of SEQ ID NO: 2, but which includes substitutions, deletions, insertions, or additions of one to 5 amino acid residues, and which has sigma S factor activity of RNA polymerase.

2. The method according to claim 1, wherein the bacterium is cultured at pH 3 to 5.

3. The method according to claim 1, wherein L-glutamic acid accumulates and precipitates in the medium during the culture.

4. The method according to claim 1, wherein the rpoS gene is inactivated by a method selected from the group consisting of reducing expression of the rpoS gene, disrupting the rpoS gene, and combinations thereof.

5. The method according to claim 1, wherein the rpoS gene is selected from the group consisting of:
   (a) the DNA comprising the nucleotide sequence of SEQ ID NO: 1, and
   (b) a DNA which is able to hybridize with a sequence complementary to the entire nucleotide sequence of SEQ ID NO: 1 under stringent conditions comprising washing at a salt concentration corresponding to 60° C., 0.1×SSC, 0.1% SDS, and wherein said DNA encodes a protein having sigma S factor activity of RNA polymerase.

6. The method according to claim 1, wherein the bacterium is *Pantoea ananatis* or *Pantoea agglomerans*.

* * * * *

SEQUENCE LISTING

<160> NUMBER OF SEQ ID NOS: 16

<210> SEQ ID NO 1
<211> LENGTH: 993
<212> TYPE: DNA
<213> ORGANISM: Pantoea ananatis
<220> FEATURE:
<221> NAME/KEY: CDS
<222> LOCATION: (1)..(993)

<400> SEQUENCE: 1

| | | | | | | | | | | | | | | | |
|---|---|---|---|---|---|---|---|---|---|---|---|---|---|---|---|
| atg | agc | cag | aat | acg | ctg | aaa | gta | aac | gag | tta | cat | gag | aac | gcg | gaa | 48 |
| Met | Ser | Gln | Asn | Thr | Leu | Lys | Val | Asn | Glu | Leu | His | Glu | Asn | Ala | Glu |
| 1 | | | | 5 | | | | | 10 | | | | | 15 | |

| ttc | gaa | gag | aat | gga | gca | gag | att | ttt | gat | gag | aag | gca | ctc | gtt | gaa | 96 |
| Phe | Glu | Glu | Asn | Gly | Ala | Glu | Ile | Phe | Asp | Glu | Lys | Ala | Leu | Val | Glu |
| | | | 20 | | | | | 25 | | | | | 30 | | |

| aat | gaa | tct | ggc | gac | aat | gat | gta | gca | gaa | gag | gag | ttg | ctg | gcg | cag | 144 |
| Asn | Glu | Ser | Gly | Asp | Asn | Asp | Val | Ala | Glu | Glu | Glu | Leu | Leu | Ala | Gln |
| | 35 | | | | | 40 | | | | | 45 | | | | |

| ggt | gcg | acg | caa | cgt | gta | ctt | gat | gct | act | caa | ctc | tat | ctt | ggg | gag | 192 |
| Gly | Ala | Thr | Gln | Arg | Val | Leu | Asp | Ala | Thr | Gln | Leu | Tyr | Leu | Gly | Glu |
| 50 | | | | | 55 | | | | | 60 | | | | | |

| att | ggc | tat | tct | cca | ttg | ctg | acg | gca | gag | gaa | gaa | gtt | ctt | ttt | gct | 240 |
| Ile | Gly | Tyr | Ser | Pro | Leu | Leu | Thr | Ala | Glu | Glu | Glu | Val | Leu | Phe | Ala |
| 65 | | | | 70 | | | | | 75 | | | | | 80 | |

| cgc | cgc | gca | tta | cga | ggt | gat | att | cct | tct | cgt | cgc | cgc | atg | atc | gaa | 288 |
| Arg | Arg | Ala | Leu | Arg | Gly | Asp | Ile | Pro | Ser | Arg | Arg | Arg | Met | Ile | Glu |
| | | | | 85 | | | | | 90 | | | | | 95 | |

| agt | aac | tta | cgc | ctg | gtg | gta | aag | att | gcc | cga | cgt | tac | agc | aat | cgc | 336 |
| Ser | Asn | Leu | Arg | Leu | Val | Val | Lys | Ile | Ala | Arg | Arg | Tyr | Ser | Asn | Arg |
| | | | 100 | | | | | 105 | | | | | 110 | | |

| ggt | ctg | gct | ctg | ctg | gac | ctg | att | gaa | gaa | ggt | aac | ctc | ggc | ctg | atc | 384 |
| Gly | Leu | Ala | Leu | Leu | Asp | Leu | Ile | Glu | Glu | Gly | Asn | Leu | Gly | Leu | Ile |
| | | 115 | | | | | 120 | | | | | 125 | | | |

| cgt | gcc | gtt | gaa | aag | ttt | gat | cca | gaa | cgt | gga | ttc | cgc | ttc | tca | acg | 432 |
| Arg | Ala | Val | Glu | Lys | Phe | Asp | Pro | Glu | Arg | Gly | Phe | Arg | Phe | Ser | Thr |
| | 130 | | | | | 135 | | | | | 140 | | | | |

| tat | gcc | acc | tgg | tgg | att | cgt | cag | acc | att | gaa | cgg | gca | atc | atg | aac | 480 |
| Tyr | Ala | Thr | Trp | Trp | Ile | Arg | Gln | Thr | Ile | Glu | Arg | Ala | Ile | Met | Asn |
| 145 | | | | | 150 | | | | | 155 | | | | | 160 |

| cag | acc | cgt | aca | att | cgt | ttg | cca | atc | cat | att | gtt | aaa | gaa | ctg | aac | 528 |
| Gln | Thr | Arg | Thr | Ile | Arg | Leu | Pro | Ile | His | Ile | Val | Lys | Glu | Leu | Asn |
| | | | | 165 | | | | | 170 | | | | | 175 | |

| gtt | tat | ctg | cgt | act | gcg | cgt | gaa | ctt | tct | cac | aag | ctt | gac | cat | gag | 576 |
| Val | Tyr | Leu | Arg | Thr | Ala | Arg | Glu | Leu | Ser | His | Lys | Leu | Asp | His | Glu |
| | | | 180 | | | | | 185 | | | | | 190 | | |

| ccg | agt | gcg | gaa | gaa | att | gca | gaa | caa | ctg | gat | aag | ccg | gtt | gat | gac | 624 |
| Pro | Ser | Ala | Glu | Glu | Ile | Ala | Glu | Gln | Leu | Asp | Lys | Pro | Val | Asp | Asp |
| | | 195 | | | | | 200 | | | | | 205 | | | |

| gtt | agt | cgt | atg | ttg | cgt | ctc | aac | gaa | cgc | att | acc | tca | gtt | gat | act | 672 |
| Val | Ser | Arg | Met | Leu | Arg | Leu | Asn | Glu | Arg | Ile | Thr | Ser | Val | Asp | Thr |
| | 210 | | | | | 215 | | | | | 220 | | | | |

| cca | ctg | gga | ggg | gat | tct | gag | aaa | gcg | ctg | ctg | gat | att | ctg | gcc | gat | 720 |
| Pro | Leu | Gly | Gly | Asp | Ser | Glu | Lys | Ala | Leu | Leu | Asp | Ile | Leu | Ala | Asp |
| 225 | | | | | 230 | | | | | 235 | | | | | 240 |

| gaa | aaa | gac | aac | ggc | cca | gaa | gac | act | acg | caa | gat | gac | gat | atg | aaa | 768 |
| Glu | Lys | Asp | Asn | Gly | Pro | Glu | Asp | Thr | Thr | Gln | Asp | Asp | Asp | Met | Lys |
| | | | | 245 | | | | | 250 | | | | | 255 | |

| caa | agt | atc | gtt | aaa | tgg | ttg | ttc | gaa | ctg | aac | gct | aag | cag | cgc | gaa | 816 |

```
Gln Ser Ile Val Lys Trp Leu Phe Glu Leu Asn Ala Lys Gln Arg Glu
            260                 265                 270 gtg ttg gct cgt cgt ttc ggc ctg ttg ggc tat gaa gcg gca acg ctc      864
Val Leu Ala Arg Arg Phe Gly Leu Leu Gly Tyr Glu Ala Ala Thr Leu
            275                 280                 285 gaa gat gtt ggc cgt gaa atc ggt tta acc cgc gag cgt gtg cgt cag      912
Glu Asp Val Gly Arg Glu Ile Gly Leu Thr Arg Glu Arg Val Arg Gln
            290                 295                 300 att cag gtt gaa ggt ttg cgc cgt ctg cgt gaa atc ctg cag ggt cag      960
Ile Gln Val Glu Gly Leu Arg Arg Leu Arg Glu Ile Leu Gln Gly Gln
305                 310                 315                 320 ggc ctc agc att gaa gca ctg ttc cgc gaa taa                          993
Gly Leu Ser Ile Glu Ala Leu Phe Arg Glu
            325                 330

<210> SEQ ID NO 2
<211> LENGTH: 330
<212> TYPE: PRT
<213> ORGANISM: Pantoea ananatis

<400> SEQUENCE: 2

Met Ser Gln Asn Thr Leu Lys Val Asn Glu Leu His Glu Asn Ala Glu
1               5                   10                  15

Phe Glu Glu Asn Gly Ala Glu Ile Phe Asp Glu Lys Ala Leu Val Glu
            20                  25                  30

Asn Glu Ser Gly Asp Asn Asp Val Ala Glu Glu Leu Leu Ala Gln
        35                  40                  45

Gly Ala Thr Gln Arg Val Leu Asp Ala Thr Gln Leu Tyr Leu Gly Glu
    50                  55                  60

Ile Gly Tyr Ser Pro Leu Leu Thr Ala Glu Glu Val Leu Phe Ala
65                  70                  75                  80

Arg Arg Ala Leu Arg Gly Asp Ile Pro Ser Arg Arg Met Ile Glu
                85                  90                  95

Ser Asn Leu Arg Leu Val Val Lys Ile Ala Arg Arg Tyr Ser Asn Arg
            100                 105                 110

Gly Leu Ala Leu Leu Asp Leu Ile Glu Glu Gly Asn Leu Gly Leu Ile
        115                 120                 125

Arg Ala Val Glu Lys Phe Asp Pro Glu Arg Gly Phe Arg Phe Ser Thr
130                 135                 140

Tyr Ala Thr Trp Trp Ile Arg Gln Thr Ile Glu Arg Ala Ile Met Asn
145                 150                 155                 160

Gln Thr Arg Thr Ile Arg Leu Pro Ile His Ile Val Lys Glu Leu Asn
                165                 170                 175

Val Tyr Leu Arg Thr Ala Arg Glu Leu Ser His Lys Leu Asp His Glu
            180                 185                 190

Pro Ser Ala Glu Glu Ile Ala Glu Gln Leu Asp Lys Pro Val Asp Asp
        195                 200                 205

Val Ser Arg Met Leu Arg Leu Asn Glu Arg Ile Thr Ser Val Asp Thr
210                 215                 220

Pro Leu Gly Gly Asp Ser Glu Lys Ala Leu Leu Asp Ile Leu Ala Asp
225                 230                 235                 240

Glu Lys Asp Asn Gly Pro Glu Asp Thr Thr Gln Asp Asp Met Lys
                245                 250                 255

Gln Ser Ile Val Lys Trp Leu Phe Glu Leu Asn Ala Lys Gln Arg Glu
            260                 265                 270

Val Leu Ala Arg Arg Phe Gly Leu Leu Gly Tyr Glu Ala Ala Thr Leu
        275                 280                 285
```

-continued

Glu Asp Val Gly Arg Glu Ile Gly Leu Thr Arg Glu Arg Val Arg Gln
            290                 295                 300

Ile Gln Val Glu Gly Leu Arg Arg Leu Arg Glu Ile Leu Gln Gly Gln
305                 310                 315                 320

Gly Leu Ser Ile Glu Ala Leu Phe Arg Glu
                325                 330

<210> SEQ ID NO 3
<211> LENGTH: 34
<212> TYPE: DNA
<213> ORGANISM: Artificial
<220> FEATURE:
<223> OTHER INFORMATION: primer Tn10-750Xho

<400> SEQUENCE: 3
tccgctcgag atctgttgtg cgtgtttaga ttgg                              34

<210> SEQ ID NO 4
<211> LENGTH: 34
<212> TYPE: DNA
<213> ORGANISM: Artificial
<220> FEATURE:
<223> OTHER INFORMATION: primer Tn10-3020Xho

<400> SEQUENCE: 4
tccgctcgag caatggctgg tttatgcata tcgc                              34

<210> SEQ ID NO 5
<211> LENGTH: 34
<212> TYPE: DNA
<213> ORGANISM: Artificial
<220> FEATURE:
<223> OTHER INFORMATION: primer pUT-3710Xho

<400> SEQUENCE: 5
tccgctcgag ctccatttta gcttccttag ctcc                              34

<210> SEQ ID NO 6
<211> LENGTH: 32
<212> TYPE: DNA
<213> ORGANISM: Artificial
<220> FEATURE:
<223> OTHER INFORMATION: primer pUT-3020Xho

<400> SEQUENCE: 6
tccgctcgag tttaaggcag ttattggtgc cc                                32

<210> SEQ ID NO 7
<211> LENGTH: 30
<212> TYPE: DNA
<213> ORGANISM: Artificial
<220> FEATURE:
<223> OTHER INFORMATION: primer rpoS-F1

<400> SEQUENCE: 7
tgaaaaactg gatgcgggcc ctgagactga                                   30

<210> SEQ ID NO 8
<211> LENGTH: 40
<212> TYPE: DNA
<213> ORGANISM: Artificial
<220> FEATURE:
<223> OTHER INFORMATION: primer rpoS-FR

<400> SEQUENCE: 8
ttcaatgctg ggcagattcc tgaggactct gccggattat 40

<210> SEQ ID NO 9
<211> LENGTH: 40
<212> TYPE: DNA
<213> ORGANISM: Artificial
<220> FEATURE:
<223> OTHER INFORMATION: primer rpoS-RF

<400> SEQUENCE: 9
ggaatctgcc cagcattgaa gcactgttcc gcgaataagc 40

<210> SEQ ID NO 10
<211> LENGTH: 30
<212> TYPE: DNA
<213> ORGANISM: Artificial
<220> FEATURE:
<223> OTHER INFORMATION: primer rpoS-R1

<400> SEQUENCE: 10
cctttatggt tgaaatgacc gagacggcca 30

<210> SEQ ID NO 11
<211> LENGTH: 40
<212> TYPE: DNA
<213> ORGANISM: Artificial
<220> FEATURE:
<223> OTHER INFORMATION: primer KpnI-rpoS-F2

<400> SEQUENCE: 11
gatcggtacc tggatgaggg ctatgtgtca gtgactgcat 40

<210> SEQ ID NO 12
<211> LENGTH: 40
<212> TYPE: DNA
<213> ORGANISM: Artificial
<220> FEATURE:
<223> OTHER INFORMATION: primer KpnI-rpoS-R2

<400> SEQUENCE: 12
gatcggtacc aaacagcctg gtcctgatgg atgaaatcgg 40

<210> SEQ ID NO 13
<211> LENGTH: 33
<212> TYPE: DNA
<213> ORGANISM: Artificial
<220> FEATURE:
<223> OTHER INFORMATION: primer 1

<400> SEQUENCE: 13
ggaagatcta tttgccttcg cacatcaacc tgg 33

<210> SEQ ID NO 14
<211> LENGTH: 30
<212> TYPE: DNA
<213> ORGANISM: Artificial
<220> FEATURE:
<223> OTHER INFORMATION: primer 2

<400> SEQUENCE: 14
cggggtacct tgtaaatatt ttaacccgcc 30

<210> SEQ ID NO 15
<211> LENGTH: 56
<212> TYPE: DNA
<213> ORGANISM: Artificial
<220> FEATURE:

```
<223> OTHER INFORMATION: primer 3

<400> SEQUENCE: 15
ggaagatcta aggagacctt aaatgagcga cacaacgatc ctgcaaaaca gtaccc        56

<210> SEQ ID NO 16
<211> LENGTH: 39
<212> TYPE: DNA
<213> ORGANISM: Artificial
<220> FEATURE:
<223> OTHER INFORMATION: primer 4

<400> SEQUENCE: 16
cggggtacct cgtagaggtt tactggcgct tatccagcg                           39
```